United States Patent
Lancaster et al.

(10) Patent No.: US 9,025,138 B2
(45) Date of Patent: May 5, 2015

(54) METHOD FOR SUPPRESSING AN ECHO SIGNAL

(75) Inventors: Gavin Lancaster, Innsbruck (AT); Konrad A. Roider, Mills (AT); Dieter Sewald, Eschen (DE)

(73) Assignee: Swarovski-Optik KG. (AT)

( * ) Notice: Subject to any disclaimer, the term of this patent is extended or adjusted under 35 U.S.C. 154(b) by 204 days.

(21) Appl. No.: 13/596,675

(22) Filed: Aug. 28, 2012

(65) Prior Publication Data

US 2013/0222783 A1 Aug. 29, 2013

(30) Foreign Application Priority Data

Aug. 29, 2011 (AT) .................................. 1232/2011

(51) Int. Cl.
*G01S 7/487* (2006.01)
*G01S 17/10* (2006.01)
*G01S 7/481* (2006.01)
*G01S 7/497* (2006.01)

(52) U.S. Cl.
CPC .............. *G01S 7/4876* (2013.01); *G01S 17/105* (2013.01); *G01S 7/4812* (2013.01); *G01S 7/497* (2013.01)

(58) Field of Classification Search
CPC ..... G01S 17/105; G01S 7/4812; G01S 7/497; G01S 13/00; G01S 13/34; G01C 3/08
USPC ............. 356/3.01–3.15, 4.01–4.1, 5.01–5.15, 356/6–22, 28, 28.5
See application file for complete search history.

(56) References Cited

U.S. PATENT DOCUMENTS

| 4,584,477 | A | * | 4/1986 | Yoshino et al. | 250/351 |
| 4,895,441 | A | * | 1/1990 | Allen, Jr. | 356/5.09 |
| 6,229,598 | B1 | | 5/2001 | Yoshida | |
| 6,650,404 | B1 | | 11/2003 | Crawford | |
| 7,599,045 | B2 | | 10/2009 | Hung | |
| 2001/0013929 | A1 | * | 8/2001 | Torsten | 356/5.01 |
| 2003/0035097 | A1 | | 2/2003 | Lai et al. | |
| 2003/0066977 | A1 | | 4/2003 | Hipp et al. | |
| 2004/0070745 | A1 | | 4/2004 | Lewis et al. | |
| 2005/0078295 | A1 | * | 4/2005 | Tansey | 356/4.1 |
| 2006/0214091 | A1 | | 9/2006 | Richter et al. | |
| 2007/0103671 | A1 | * | 5/2007 | Ash | 356/139.01 |
| 2008/0143998 | A1 | | 6/2008 | Hung | |
| 2012/0268727 | A1 | | 10/2012 | Schrey et al. | |

FOREIGN PATENT DOCUMENTS

| DE | 10153742 A1 | 5/2003 |
| DE | 102008018718 A1 | 10/2009 |
| EP | 1288676 A1 | 3/2003 |
| EP | 1901092 A2 | 3/2008 |
| WO | 2005054902 A1 | 6/2005 |
| WO | 2009094687 A2 | 8/2009 |

* cited by examiner

*Primary Examiner* — Luke Ratcliffe
(74) *Attorney, Agent, or Firm* — Lerner, David, Littenberg, Krumholz & Mentlik, LLP

(57) ABSTRACT

Method for suppressing an echo signal in a range finder device, which has at least one light-sensitive receiver and at least one laser light source as transmitter, characterized in that at least one counter signal corresponding to the echo signal is generated and which counter signal is super-imposed to a signal generated by the transmitter.

13 Claims, 1 Drawing Sheet

METHOD FOR SUPPRESSING AN ECHO SIGNAL

CROSS-REFERENCE TO RELATED APPLICATION

The present application claims priority from A 1232/2011 filed Aug. 29, 2011, the disclosure of which is hereby incorporated herein by reference.

BACKGROUND

The invention relates to a method for suppressing an echo signal in a range finder device, which has at least one light-sensitive receiver and at least one laser light source as a transmitter, with the echo signal to be suppressed being a result of diffuse reflectances of the light emitted by the transmitter at surfaces before the actual target—for example at components of the optical signal path.

Furthermore, the invention relates to a range finder device having at least one light-sensitive receiver and at least one laser light source as transmitter.

In addition, the invention relates to a far-optical device, in particular a telescope or a telescopic sight.

Range finder devices of the generic kind, also referred to as laser range finder, perform a range finding by a laser pulse or pulse trains being emitted by a transmitter, being reflected by the target object, being detected by a receiver and the period of time and thus the covered distance is determined by means of the delay between the transmission pulses and the receiving pulses.

Transmitter and receiver of a range finder device of the generic kind can be arranged at least partially in one optical path. If transmitter and receiver are arranged within one and probably even attached to one and the same (prism) optics, as for example known from document WO 2009094687 A2, it can occur that a small portion of the laser pulses emitted by the transmitter reach the sensitive receiver directly due to internal scattering, reflection etc. thus generating a test signal. This incorrect test signal is usually larger than the signals from a target object further away and therefore interfere with/manipulate the measurement. Since said flare is almost always present at first, only measurements within the close range (up to some 100 m) are affected. The term interfering echo signal in this document refers to all portions of the light emitted by the transmitter, which portions have arrived at the receiver due to internal reflections, scatterings or other parasitic errors.

The optical cross talk can be influenced by constructional measures (e.g. diaphragms, geometry). In terms of electronics this can be defined by e.g. a first time window, when e.g. the receiver and the amplifier are not active, since the cross talker is present here. Only after this window has expired, a range finding is carried out. The disadvantage is here that within this window, no measurement can be carried out at all. In the document U.S. Pat. No. 7,599,045 B2, this 'blind' window is realized by the detecting signal inverting the portion branched off and lying within said window and adding it to the test signal again, with the result that the sum signal is zero again. The disadvantage of the known embodiment is that due to the 'blind' window only ranges of considerably more than 100 m can be measured.

BRIEF SUMMARY OF THE INVENTION

The underlying objective of the invention is therefore to minimize the influence of the optical cross talk by electronic measures to such an extent that a range finding is also allowed for shorter measuring distances (<100 m) without suppressing the useful echo in an inadmissible way.

According to the invention, this objective is achieved by using a method of the above mentioned kind by generating at least one counter signal corresponding to the echo signal which counter signal is super-imposed to a signal generated by the transmitter. By super-imposing the counter signal, the proportion of the cross talk is specifically reduced, thus increasing the reliability of measurement in an easy way.

According to the preferred embodiment of the invention, the signal generated by the transmitter and the counter signal are subtracted from each other. In this way, parasitic errors can be easily reduced or eliminated. For achieving a good signal-to-noise ratio it is furthermore possible for a resulting differential input of the signal generated by the transmitter and the counter signal to be intensified.

According to another preferred embodiment of the invention, a height and/or a value and/or amplitude and/or a pulse shape of the counter signal can be varied by a calibrating step. According to an advantageous variant, the calibrating step can be carried out at the beginning of each range finding. Since this is a variable compensation, also cross talks changing over time can be compensated.

A particular advantageous embodiment provides that a signal vector of the resulting signal is analyzed within the scope of the calibrating step. Thus, a particular reliable calibrating can be ensured.

The quality of the measuring accuracy that can be obtained by using the range finder device can additionally be improved by repeating the calibrating step several times.

The objective mentioned above can according to the invention also be achieved by a range finder device of the kind referred to at the beginning by the fact that it is configured to generate a counter signal corresponding to an echo signal which counter signal is super-imposed to a signal generated by the transmitter.

According to an advantageous further embodiment of the invention, the range finder device can be configured to subtract the signal generated by the receiver and the counter signal from each other.

Another very advantageous variant of the invention provides that the range finder device is configured to intensify a differential input resulting from the echo signal and the counter signal.

According to a particular advantageous further embodiment of the invention it is furthermore possible for the range finder device to be configured to vary a height and/or a value and/or an amplitude and/or a pulse shape of the counter signal in one calibrating step.

According to a preferred embodiment of the invention, the range finder device can be configured to carry out the calibrating step at the beginning of the range finding. It can furthermore be provided that the range finder device is configured to analyze a signal vector of a resulting differential input within the scope of the calibrating step.

Furthermore, the range finder device can be adapted to repeat the calibrating step several times.

The objective mentioned above can also be achieved by a far-optical device of the kind mentioned above, including a range finder device according to the invention, with transmitter and receiver being at least partially disposed within the identical optical path.

The invention including further advantages will be explained in more detail below by means of non-restricting exemplary embodiments, which are shown in the drawings:

BRIEF DESCRIPTION OF THE DRAWINGS

The heavily simplified schematics show.

DETAILED DESCRIPTION

Figure 1:
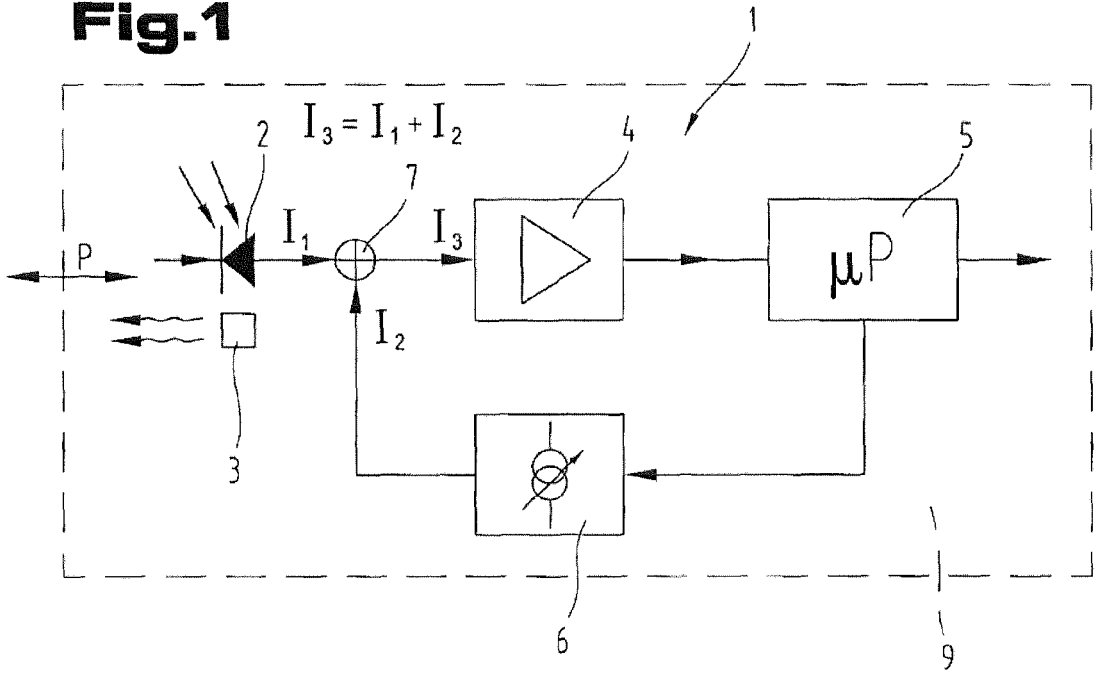
FIG. 1 a block diagram of a range finder device according to the invention.

Firstly, it should be pointed out that the same parts described in the different embodiments are denoted by the same reference numbers and the same component names and the disclosures made throughout the description can be transposed in terms of meaning to same parts bearing the same reference numbers or same component names. Furthermore, the positions chosen for the purposes of the description, such as top, bottom, side, etc., relate to the drawing specifically being described and can be transposed in terms of meaning to a new position when another position is being described. Individual features or combinations of features from the different embodiments illustrated and described may be construed as independent inventive solutions or solutions proposed by the invention in their own right.

According to the embodiment of the invention shown in FIG. 1, the range finder device according to the invention can have a light-sensitive receiver 2 and a laser light source as transmitter 3. Transmitter 3 and receiver 2 can partially or completely be located in or extend through one optical path, which is indicated by a double arrow and the letter P in FIG. 1. This means, the transmitters and receivers can be arranged coaxially. The receiver can be embodied as a photodiode, for example as avalanche diode. As it can be furthermore seen in FIG. 1, the range finder device can be disposed in or at a far-optical device 9.

The electrical signal (current) 11 generated by the receiver/detector2 (avalanche diode) is intensified by means of an amplifier 4 and analyzed by a microprocessor 5. Instead of a microprocessor, also a signal processor or another appropriate circuit can be provided. Furthermore, a controlled power source 6 for generating a signal or current 12 is provided.

Prior to the amplifier 4, a summation node 7 is disposed, where the signals 11+12 are super-imposed to be signal 13, so that 13=11+12 applies.

In the known manner, the microprocessor 5 determines the temporal position of the reflected (light) pulses emitted by the sender 3 and calculates the range 13 to the target therefrom. Since the reflected pulses are usually very small and contaminated by much background noise, a complete pulse train (up to some 1000 pulses) is analyzed by averaging in order to improve the signal-to-noise ratio.

Figure 2:
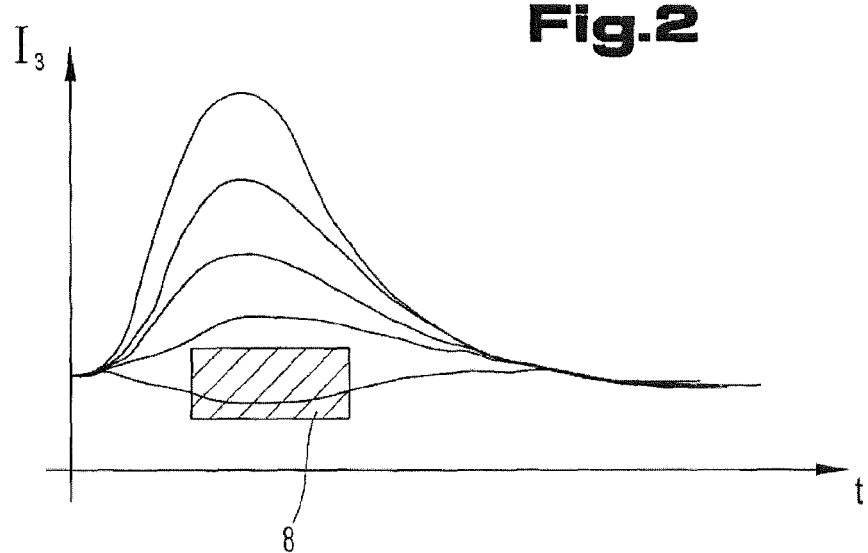
FIG. 2 the signal pattern of a signal resulting from a superimposition between an echo signal and a counter signal.

Now, the first pulses of each measurement are used to determine the proportion of the optical cross talk (echo signal). For this purpose, the microprocessor 5 analyzes, as shown in FIG. 2, a very early temporal window, where a portion of the optical cross talk (echo signal) is present. Using this information regarding the signal level in this time window, a counter pulse is generated via the controlled power source 6, which counter pulse is superimposed prior to the amplifier thus reducing the proportion of the cross talk (echo signal). The microprocessor again analyzes this new signal 13 in this time window 8 and checks whether the signal 13 has reduced within this time window. Should it remain too large, the process is repeated (up to a maximum number of cycles, which are essentially exclusively limited by the available measurement duration) under a further adaption of the pulse level and the temporal position of the counter pulse 12. In other words, it is checked whether the level of the signal 13 within the time window 8 corresponds to a threshold value for the signal level of the signal 13, which would correspond to a state not disturbed by reflections, scattered light etc. by the transmitter. The signal 13 is thus controlled by modifying the signal 12 towards threshold value. In this way, the echo signal can be suppressed or compensated prior to the analysis of the signal in the microprocessor 5.

Figure 3:
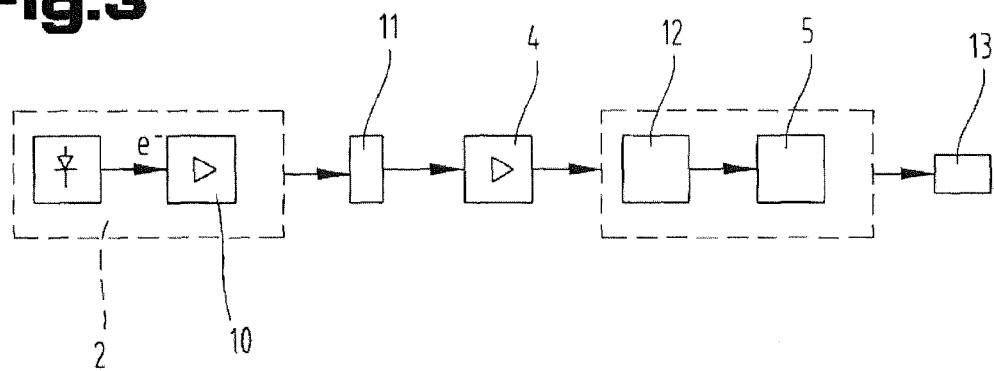
FIG. 3 a block diagram of another embodiment of the invention.

As shown in FIG. 3, the receiver 2 can have an internal amplifier 10 additional to the (avalanche-) photodiode. In a step 11, the signal 11 and/or the counter signal 12 and/or the signal 13 can be subject to a pulse width modulation (PWM) and/or an impedance matching and/or a filtration, before they are fed into the amplifier 4. Furthermore, a digital analog converter 12 can be installed prior to the microprocessor 5.

FIG. 2 shows the current 13 after the summation. The window 8, where the sum signal 13 is to be, is shown in a hatched way. The larger graph in FIG. 2 is without compensation, and then the calibrating steps follow by getting smaller each, until the lowest graph then lies within the window=>calibration finished.

When the calibrating process has been finished, the actual measurement takes place. This has the advantage that after compensating the cross talk measurements are also allowed with short periods of time (short ranges) and since, if a compensation is calibrated prior to each measurement, temporal changing cross talks (e.g. caused by finger prints on the front lens, depositing dust particles, slightly changing optical paths due to mechanical or terminal influences, changing pulse amplitude of the transmitter) can also be taken into consideration. It is generally also possible for the pulse shape to be created the in the closed loop in a variable way and to be assimilated to the closed loop for compensation.

Alternatively or in addition to the above mentioned closed loop control, it is possible to use an avalanche photodiode, the bias voltage of which can be modified in such a way that it is not "loaded" during the beginning of the range finding and does essentially not emit measuring signals. In a time period that can be preselected after the beginning of the measurement, the bias voltage could be increased in such a way that the avalanche photodiode is sensitive enough for detecting the light pulse reflected by the target.

Alternatively or additionally to the embodiments mentioned in the last paragraph, it would also be possible for the magnification factor of at least one of the steps of the amplifier 4 to be varied depending on time, with the result that no signal gain could take place at the beginning of the measurement and the intensity could be increased within a defined period of time after the beginning of the measurement.

LIST OF REFERENCE NUMERALS

1 Range finder device
2 Receiver
3 Transmitter
4 Amplifier
5 Microprocessor
6 Power source
7 Summation node
8 Time window
9 Far-optical device
10 Internal amplifier
11 Pulse width modulator
12 Analog digital converter
13 Range to target

The invention claimed is:

1. A method for suppressing an echo signal caused by optical cross talk in a range finder device, which has at least one light-sensitive receiver and at least one laser light source as transmitter, the method comprising:
  generating at least one counter signal corresponding to the echo signal caused by optical cross talk; and
  super-imposing, in an additive or subtractive way, the at least one counter signal to a signal generated by the receiver, forming a resulting signal.

2. The method according to claim 1, wherein the resulting signal is intensified.

3. The method according to one of the claim 1, further comprising a calibrating step, wherein a level and/or a value and/or an amplitude and/or a pulse shape of the at least one counter signal are varied.

4. The method according to claim 3, wherein the calibrating step is carried out prior to the range finding step.

5. The method according to claim 3, wherein within the scope of the calibrating step, a signal vector of the resulting signal is analyzed.

6. The method according to claim 3, wherein the calibrating step is repeated several times.

7. A range finder device having comprising:
  at least one light-sensitive receiver; and
  at least one laser light source as transmitter;
  wherein the range finder device is adapted to generate at least one counter signal corresponding to an echo signal caused by optical cross talk and which the at least one counter signal is super-imposed, in an additive or subtractive way, to a signal generated by the receiver, forming a resulting signal.

8. The range finder device according to claim 7, wherein it is adapted to intensify the resulting signal.

9. The range finder device according to claim 7, wherein it is adapted to vary a level and/or a value and/or an amplitude and/or a pulse shape of the at least one counter signal in one calibrating step.

10. The range finder device according to claim 9, wherein it is adapted to carry out the calibrating step prior to the range finding.

11. The range finder device according to claim 9, wherein it is adapted to analyze a signal vector of the resulting signal within the scope of the calibrating step.

12. The range finder device according to claim 9, wherein it is adapted to repeat the calibrating step several times.

13. A far-optical device comprising a range finder device according to claim 7, with transmitter and receiver being at least partially disposed in one optical path.

\* \* \* \* \*

UNITED STATES PATENT AND TRADEMARK OFFICE
CERTIFICATE OF CORRECTION

| | | |
|---|---|---|
| PATENT NO. | : 9,025,138 B2 | Page 1 of 1 |
| APPLICATION NO. | : 13/596675 | |
| DATED | : May 5, 2015 | |
| INVENTOR(S) | : Gavin Lancaster, Konrad A. Roider and Dieter Sewald | |

It is certified that error appears in the above-identified patent and that said Letters Patent is hereby corrected as shown below:

Title Page, Item (75) Inventors:, "Sewald, Eschen (DE)" should read --Sewald, Eschen (LI)--.

Signed and Sealed this
Eighth Day of September, 2015

Michelle K. Lee
*Director of the United States Patent and Trademark Office*